United States Patent [19]

Senda et al.

[11] 4,443,607

[45] Apr. 17, 1984

[54] 1(2H)-ISOQUINOLONE COMPOUNDS AND ACID ADDITION SALTS THEREOF

[75] Inventors: Shigeo Senda; Osamu Ohtani, both of Gifu; Eiichi Katho; Mitsuaki Nagasaka, both of Aichi; Hidekazu Miyake, Tokushima; Khosuke Fujiwara, Tokushima; Motoaki Tanaka, Tokushima, all of Japan

[73] Assignees: Maruko Seiyaku Co., Ltd., Aichi; Taiho Pharmaceutical Co., Ltd., Tokyo, both of Japan

[21] Appl. No.: 361,935

[22] Filed: Mar. 25, 1982

[30] Foreign Application Priority Data

Mar. 28, 1981 [JP]  Japan .................................. 56-44700
Mar. 4, 1982 [JP]  Japan .................................. 57-33015

[51] Int. Cl.$^3$ ........................................ C07D 217/24
[52] U.S. Cl. .................................. 546/141; 544/128; 544/363
[58] Field of Search ................. 546/141; 544/128, 363

[56] References Cited

FOREIGN PATENT DOCUMENTS 3031574  3/1981  Fed. Rep. of Germany .
2058783  4/1981  United Kingdom .

OTHER PUBLICATIONS

Senda et al., Chem. Abstr. 132692, vol. 95, (1981).

*Primary Examiner*—John M. Ford
*Assistant Examiner*—Bernard Dentz
*Attorney, Agent, or Firm*—Sughrue, Mion, Zinn, Macpeak & Seas

[57] ABSTRACT

Novel 1(2H)-isoquinolone compounds and the acid addition salts thereof are disclosed. These compounds are useful as pharmaceutical agents in view of their anti-ulcer, stomach mucous membrane blood flow increasing, anti-hypertensive, analgesic, anti-histamine, anti-cholinergic and gastric secretion inhibitory activities.

4 Claims, No Drawings

1(2H)-ISOQUINOLONE COMPOUNDS AND ACID ADDITION SALTS THEREOF

BACKGROUND OF THE INVENTION

1. Field of the Invention

This invention relates to novel 1(2H)-isoquinolone compounds and the acid addition salts thereof which exhibit useful anti-ulcer activity, blood flow increasing activity in stomach mucous membrane, anti-hypertensive activity, analgesic activity, anti-histamine activity, anti-cholinergic activity and gastric secretion inhibitory activity in mammals.

2. Description of the Prior Art

Hitherto, a wide variety of 1(2H)-isoquinolone compounds were known to have various pharmacological activities. For example, Coyne et al. U.S. Pat. No. 3,600,394 discloses 2-aminoalkyl-3-substituted-phenyl-1(2H)-isoquinolones having anti-inflammatory and anti-microbial activities; Japanese patent publication (Unexamined) No. 122,075/76 and German OLS No. 2,702,600 disclose 7-substituted-3-substituted-phenyl-1(2H)-isoquinolone compounds useful as, for example, anti-convulsant and anti-hypertensive agents. However, these known compounds are different from the compounds of the present invention in their activities and/or chemical structures.

The present inventors have previously found that certain type of 1(2H)-isoquinolone compounds have excellent analgesic, gastric secretion inhibitory, anti-depressant, anti-histamine, anti-cholinergic and anti-ulcer activities as disclosed in U.S. patent application Ser. No. 182,188 filed Aug. 28, 1980 now U.S. Pat. No. 4,393,210. As a result of further studies, the present inventors have also found that the 1(2H)-isoquinolone compounds and the acid addition salts thereof according to the present invention are useful as pharmaceutical agents.

SUMMARY OF THE INVENTION

The present invention is therefore to provide novel 1(2H)-isoquinolone compounds represented by the formula (I) hereinafter described and the acid addition salts thereof which are useful pharmaceutical agents.

DETAILED DESCRIPTION OF THE INVENTION

The 1(2H)-isoquinolone compounds of the present invention can be represented by the formula (I):

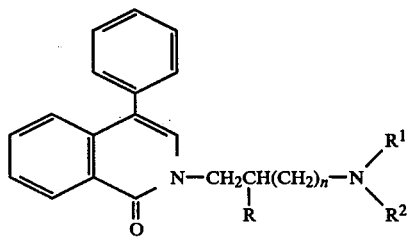

wherein n is 0 or an integer of 1, R represents a methyl group or a hydroxy group, $R^1$ represents a hydrogen atom, an alkyl group having 1 to 4 carbon atoms, an alkenyl group having 3 to 4 carbon atoms or an alkynyl group having 3 to 4 carbon atoms, and $R^2$ represents a hydrogen atom, an alkyl group having 1 to 4 carbon atoms, an alkenyl group having 3 to 4 carbon atoms, an alkynyl group having 3 to 4 carbon atoms, a benzyl group, an ethoxycarbonyl group, a mono- or dialkylcarbamoyl group having 1 to 4 carbon atoms in each alkyl group, an acetyl group, a mono- or dialkylaminoethoxyacetyl group or a group of the formula

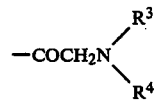

wherein $R^3$ and $R^4$, which may be the same or different, each represents a hydrogen atom, an alkyl group having 1 to 4 carbon atoms, a hydroxyalkyl group having 2 to 4 carbon atoms or an allyl group, or $R^3$ and $R^4$, when taken together with the nitrogen atom to which they are attached, represent a heterocyclic group, with the proviso that, when R represents a methyl group, both $R^1$ and $R^2$ can not be an alkyl group and that, when R represents a hydroxy group, n represents an integer of 1; and acid addition salts thereof.

The 1(2H)-isoquinolone compounds of the formua (I) above and the acid addition salts thereof exhibit excellent anti-ulcer, stomach mucous membrane blood flow increasing, anti-hypertensive, analgesic, anti-histamine, anti-cholinergic and gastric secretion inhibitory activities and, therefore, are useful as pharmaceutical agents.

The term "alkyl group" as used herein means a straight or branched chain alkyl group having 1 to 4 carbon atoms and includes methyl, ethyl, n-propyl, isopropyl, n-butyl, sec-butyl and tert-butyl groups.

The term "alkenyl group" as used therein means an alkenyl group having 3 to 4 carbon atoms and includes, for example, allyl, 2-butenyl groups and the like.

The term "alkynyl group" as used herein means an alkynyl group having 3 to 4 carbon atoms and includes, for example, 2-propynyl group and the like.

The term "heterocyclic group" as used herein for the group $—NR^3R^4$ means a 5- or 6-membered heterocyclic group which contains nitrogen atom(s) or nitrogen and oxygen atoms as hetero atoms and which may be substituted with an alkyl group having 1 to 4 carbon atoms. Preferred examples of heterocyclic groups are a pyrrolidino group, a piperazino group, a 4-methylpiperazino group, a piperidino group and a morpholino group.

The term "acid addition salts thereof" as used herein for the compounds of the formula (I) means pharmaceutically acceptable acid addition salt of inorganic or organic acids such as hydrochloride, sulfate, hydrobromide, methanesulfonate, maleate, tartrate, citrate, lactate and the like.

The 1(2H)-isoquinolone compounds of the formula (I) can be prepared by various procedures depending upon the type of the amino group $—NR^1R^2$.

The compounds of the formula (I) wherein $—NR^1R^2$ represents an amino group ($—NH_2$) or a benzylamino group can be prepared by heat-melting a 2-(chloroalkyl)-1(2H)-isoquinolone together with benzylamine in an inert atmosphere such as in a nitrogen stream for a period of about 1 to about 5 hours to obtain a corresponding 2-(benzylaminoalkyl)-1(2H)-isoquinolone.

The compounds of the formula (I) wherein $—NR^1R^2$ is an amino group can then be prepared by catalytically reducing the resulting 2-(benzylaminoalkyl)-1(2H)-isoquinolone in a solvent such as a mixture of glacial acetic acid and ethanol in the presence of a catalyst such as palladium-carbon, platinum oxide, palladium oxide and the like, while introducing hydrogen gas into the reaction mixture at a temperature of from room temperature (i.e., about 15° to about 30° C.) to about 80° C. under atmospheric pressure.

The reaction between the 2-(chloroalkyl)-1(2H)-isoquinolone and benzylamine can be preferably conducted using about 1.8 to 2 mols of benzylamine per mol of the 2-(chloroalkyl)-1(2H)-isoquinolone.

The compounds of the formula (I) wherein —NR$^1$R$^2$ represents an ethoxycarbonylamino group can be prepared by reacting the 2-(aminoalkyl)-1(2H)-isoquinolone compound prepared as described above with ethyl chlorocarbonate in a solvent such as ethanol, isopropanol and the like, in the presence of a basic catalyst such as potassium carbonate, sodium carbonate and the like, at room temperature. The reaction is preferably conducted using about 1.5 to 2 mols of ethyl chlorocarbonate per mol of the 2-(aminoalkyl)-1(2H)-isoquinolone compound for a period of about 1 to about 5 hours.

The compounds of the formula (I) wherein —NR$^1$R$^2$ represents an N'-alkylureido or N',N'-dialkylureido group, i.e., the compounds wherein R$^1$ represents a hydrogen atom and R$^2$ represents a mono- or dialkylcarbamoyl group, can be prepared by reacting the 2-(aminoalkyl)-1(2H)-isoquinolone compound prepared as described above with an isocyanate such as methyl isocyanate, ethyl isocyanate and the like, or a carbamyl chloride such as dimethylcarbamyl chloride, diethylcarbamyl chloride and the like, in a solvent such as benzene, toluene and the like at room temperature.

The reaction is preferably conducted using about 1 to about 1.4 mols of an isocyanate or carbamyl chloride per mol of the 2-(aminoalkyl)-1(2H)-isoquinolone compound for a period of from about 1 to about 5 hours.

The compounds of the formula (I) wherein —NR$^1$R$^2$ represents an acetamido group can be prepared by reacting the 2-(aminoalkyl)-1(2H)-isoquinolone prepared as described above with acetic anhydride in glacial acetic acid at room temperature to an elevated temperature (e.g., up to about 100° C.) in a molar ratio of about 1.5 to about 5 mols of acetic anhydride per mol of 2-(aminoalkyl)-1(2H)-isoquinolone for a period of from about 1 to about 5 hours.

The compounds of the formula (I) wherein —NR$^1$R$^2$ group represents an aminoethoxyacetamido group can be prepared by reacting the 2-(aminoalkyl)-1(2H)-isoquinolone with chloroacetyl chloride in a solvent such as dichloromethane, chloroform and the like in the presence of a basic catalyst such as sodium hydroxide, sodium carbonate and the like, at a temperature of from about 0° to about 10° C. for a period of from about 1 to about 5 hours, using about 1 to about 1.5 mols of chloroacetyl chloride per mol of the 2-(aminoalkyl)-1(2H)-isoquinolone to obtain a corresponding 2-(chloroacetamidoalkyl)-1(2H)-isoquinolone, and then reacting the 2-(chloroacetamidoalkyl)-1(2H)-isoquinolone with a sodium mono- or dialkylaminoethylate such as sodium dimethylaminoethylate, sodium diethylaminoethylate, sodium isopropylaminoethylate and the like in a solvent such as dichloromethane, chloroform and the like at room temperature for a period of about 24 to about 48 hours using about 1.5 to about 2 mols of a sodium mono- or dialkylaminoethylate per mol of the 2-(chloroacetamidoalkyl)-1(2H)-isoquinolone.

The compounds of the formula (I) wherein —NR$^3$R$^4$ group represents an amino group (—NH$_2$) can be prepared by subjecting the 2-(chloroacetamidoalkyl)-1(2H)-isoquinolone prepared as described above to the Gabriel reaction. More specifically, the desired compound can be obtained by heating a mixture of a 2-(chloroacetamidoalkyl)-1(2H)-isoquinolone, phthalimide and potassium carbonate in a solvent such as dimethylformamide at a temperature of about 80° C. for a period about 5 to about 10 hours to obtain a 2-(phthalimidoacetamidoalkyl)-1(2H)-isoquinolone, reacting the resulting compound with hydrazine in a solvent such as ethanol, isopropanol and the like, while heating at reflux for a period of about 5 to about 10 hours, and, after allowing the reaction mixture to cool, adding concentrated hydrochloric acid to the reaction mixture, followed by stirring at room temperature. In the above reaction, phthalimide is used in an amount of about 1.2 to 1.5 mols per mol of the 2-(2-chloroacetamidoalkyl)-1(2H)-isoquinolone and hydrazine is used in an amount of from about 2 to about 4 mols per mol of 2-(phthalimidoacetamidoalkyl)-1(2H)-isoquinolone.

The compounds of the formula (I) wherein —NR$^3$R$^4$ group represents an alkylamino group, a hydroxyalkylamino group, an allylamino group, a heterocyclic group or other groups can be prepared by reacting the 2-(chloroacetamidoalkyl)-1(2H)-isoquinolone with one of the desired amines to be introduced, for example, dimethylamine, diethylamine, diethanolamine, diallylamine, morpholine, 4-methylpiperazine, pyrrolidine, piperidine and the like, in the presence of a solvent such as methanol, ethanol, benzene and the like. The reaction conditions used in the above reaction generally vary widely depending upon the type of amine used, but the reaction is usually conducted using about 3 to about 5 mols of an amine per mol of the 2-(chloroacetamidoalkyl)-1(2H)-isoquinolone for a period of from about 2 to about 10 hours while heating at refluxing temperature of the reaction mixture.

The compounds of the formula (I) wherein R$^1$ represents a hydrogen atom, an alkyl group, an alkenyl group or an alkynyl group and R$^2$ represents an alkyl group, an alkenyl group, an alkynyl group or a benzyl group can be prepared by reacting a 2-(haloalkyl)-1(2H)-isoquinolone with an amine corresponding to the group —NR$^1$R$^2$ in the presence or absence of a catalyst such as copper powder, potassium carbonante, potassium iodide, sodium iodide, etc. while heating at a temperature of about 120° C. to about 160° C. for a period of about 1 to about 30 hours. The reaction can be conducted using a reaction solvent such as methyl ethyl ketone, dimethylformamide, xylene, tetralin and the like or using an amine as a reactant in an excess amount to serve as both the reactant and the reaction solvent. If the amine used has a low boiling point, the reaction is preferably conducted in a sealed vessel.

The compounds of the formula (I) wherein R represents a hydroxy group can be prepared by reacting 4-phenyl-1(2H)-isoquinolone with epichlorohydrin or epibromohydrin in a solvent such as dimethylformamide, toluene, xylene and the like in the presence of a catalyst such as sodium hydroxide, potassium hydroxide, sodium hydride and the like, at a temperature of from room temperature to an elevated temperature, e.g., about 80° C. to 150° C., for a period of about 4 to about 16 hours to obtain a 2-(2,3-epoxypropyl)-1(2H)-isoquinolone and then reacting the resulting epoxy compound with an amine compound in a solvent such as ethanol, dimethylformamide and the like at a temperature of about 70° C. to about 100° C. for a period of from about 3 to about 10 hours.

The starting material used in the present invention, 2-(haloalkyl)-1(2H)-isoquinolones, can be prepared by reacting known 4-phenyl-1(2H)-isoquinolone with a hydroxyalkyl halide, preferably chloride or bromide, in a molar ratio of about 1 to 1.5 mol of the hydroalkyl halide per mol of the 4-phenyl-1(2H)-isoquinolone. The reaction can be conducted in an organic solvent such as dimethylformamide, toluene, xylene and the like in the presence of a basic catalyst such as potassium carbonate, sodium carbonate, sodium hydride, calcium hydride and the like in an amount of at least 2 mols per mol of the 4-phenyl-1(2H)-isoquinolone, while heating at a temperature of about 80° to 140° C. for a period of about 1 to about 5 hours to obtain a corresponding 2-(hydroxyalkyl)-1(2H)-isoquinolone compound of the formula

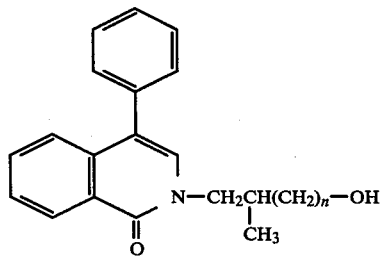
(II)

wherein n is as defined above, and the resulting 2-(hydroxyalkyl)-1(2H)-isoquinolone compound is then reacted with a halogenating agent, for example, thionyl chloride, oxalyl chloride, phosphorus oxychloride, phoshorus oxybromide and the like, while heating at refluxing temperature of the reaction mixture for a period of about 30 minutes to about 2 hours, in the presence or absence of a solvent such as benzene, carbon tetrachloride and the like.

The dose level of the compounds of the present invention as pharmaceutical agents varies depending upon the severity of conditions to be treated, the age of patients, the type of diseases or other factors, but generally ranges from about 0.5 mg to about 50 mg/kg of body weight per day in adult human administered as a single dose or multiple dose (divided into 2 to 3 doses).

The compounds of this invention can be administered orally, parenterally or intrarectally in various dosage forms such as tablets, capsules, granules, powders, injections, suppository and the like.

The above preparations can be formulated as compositions comprising suitable carriers or excipients by the procedure generally used in preparing pharmaceutical compositions.

The tablets, capsules, granules, powders, etc. for oral administration can be prepared using excipients generally used in the art, for example, calcium carbonate, calcium phosphate, starch, sucrose, lactose, talc, magnesium stearate, gelatin, polyvinylpyrrolidone, gum arabic, sorbitol, crystalline cellulose, polyethylene glycol, carboxymethylcellulose, silica and the like. Also, tablets and granules can be coated according to the method well known in the art.

The injections can be aqueous or oily suspensions, solutions or powder filled in ampoules or freeze-dried preparation which is instantly dissolved in a liquid medium just before use, and these preparations can be prepared according to the procedures well known in the art.

The suppositories can contain well-known carriers, for example, polyethylene glycol, lanolin, cacao butter, fatty acid triglycerides and the like.

The compounds of the formula (I) are generally obtained in the form of free base and, if desired, the free base can be easily converted into their acid addition salts by a conventional procedure well known in the art, for example, by reacting the free base with a pharmaceutically acceptable inorganic or organic acid in a solvent such as ethanol, ethyl acetate, acetone and the like, or reacting the free base with an aqueous solution of a pharmaceutically acceptable inorganic or organic acid at room temperature or an elevated temperature.

The present invention is further illustrated in greater detail by the following Examples and Reference Examples, but they are not to be construed as limiting the present invention. Unless otherwise indicated, all parts, percents, ratios and the like are by weight.

EXAMPLE 1

A. 44.2 g of 4-phenyl-1(2H)-isoquinolone and 55.2 g of potassium carbonate were mixed with 250 ml of dimethylformamide, and the mixture was heated at 110° C. to 120° C. for 2 hours. Thereafter, 35 g of 70% 1-chloro-2-propanol was added dropwise to the mixture, and then the resulting mixture was stirred and heated for 5 hours. After allowing the mixture to cool, the reaction mixture was poured into ice-water, and the precipitated crystals were collected by filtration, washed with water and then dried. The crystals were recrystallized from a mixture of methanol and diethyl ether to obtain 45.2 g (81% yield) of 2-(2-hydroxypropyl)-4-phenyl-1(2H)-isoquinolone having a melting point of 162° C. as colorless needles.

Elementary Analysis:
Calcd for $C_{18}H_{17}NO_2$=Molecular Weight 279.342: C, 77.40; H, 6.13; N, 5.01 (%), Found: C, 77.52; H, 6.12; N, 4.94 (%).

B. 18 g of thionyl chloride was added dropwise to a mixture of 27.9 g of 2-(2-hydroxypropyl)-4-phenyl-1(2H)-isoquinolone prepared as described above, 11.1 g of triethylamine and 200 ml of benzene and then the resulting mixture was stirred at 50° to 60° C. for 1 hour. After allowing the mixture to cool, water was added to the mixture which was then thoroughly shaked. The benzene layer was separated and dried over sodium sulfate. The solvent was distilled off, and the resulting crystals were recrystallized from a mixture of chloroform and petroleum ether to obtain 25.3 g (85% yield) of 2-(2-chloropropyl)-4-phenyl-1(2H)-isoquinolone having a melting point of 141° C. as colorless needles.

Elementary Analysis:
Calcd for $C_{18}H_{16}ClNO$=297.787: C, 72.60; H, 5.42; N, 4.70 (%), Found: C, 72.46; H, 5.50; N, 4.66 (%).

C. 14.9 g of 2-(2-chloropropyl)-4-phenyl-1(2H)-isoquinolone prepared as described above and 0.4 g of copper powder were mixed with 40 ml of diallylamine, and the mixture was heated at reflux for 5 hours in a nitrogen stream. After allowing the mixture to cool, ethyl acetate was added to the reaction mixture and the mixture was filtered. The filtrate was concentrated under reduced pressure, and the residue was dissolved in dichloromethane. The solution was washed successively with a 10% aqueous solution of sodium hydroxide and water, and dried over sodium sulfate. The solvent was distilled off and the resulting oily substance was dissolved in 80 ml of ethyl acetate. 4 g of maleic acid was added to the solution and the mixture was warmed while stirring.

The crystals precipitated after cooling were filtered and recrystallized from a mixture of ethanol and diethyl ether to obtain 15.9 g (67% yield) of 2-(2-N,N-diallylaminopropyl)-4-phenyl-1(2H)-isoquinolone maleate having a melting point of 153° C. as colorless prisms.

Elementary Analysis:
Calcd for $C_{24}H_{26}N_2O \cdot C_4H_4O_4 = 474.562$: C, 70.87; H, 6.37; N, 5.90 (%), Found: C, 70.78; H, 6.41; N, 5.96 (%).

EXAMPLE 2

A. 22 g of 4-phenyl-1(2H)-isoquinolone, 4.1 g of epichlorohydrin and 4.3 g of sodium hydride were added to 500 ml of dimethylformamide, and the mixture was stirred overnight at room temperature. Thereafter, the solvent was distilled off, and chloroform and water were added to the residue. The mixture was thoroughly shaked, and the chloroform layer was separated and dried over magnesium sulfate. The solvent was distilled off, and the residue was recrystallized from ethyl acetate to obtain 22 g (80% yield) of 2-(2,3-epoxypropyl)-4-phenyl-1(2H)-isoquinolone having a melting point of 148° C. as colorless needles.

Elementary Analysis:
Calcd for $C_{18}H_{15}NO_2 = 277.326$: C, 77.96; H, 5.45; N, 5.05 (%), C, 77.81; H, 5.47; N, 4.96 (%).

B. A mixture of 5.5 g of 2-(2,3-epoxypropyl)-4-phenyl-1(2H)-isoquinolone, 10 ml of diallylamine and 20 ml of ethanol was heated at reflux for 6 hours. Thereafter, the solvent was distilled off, and the resulting residue was recrystallized from a mixture of diethyl ether and petroleum ether to obtain 5.8 g (77% yield) of 2-(3-N,N-diallylamino-2-hydroxypropyl)-4-phenyl-1(2H)-isoquinolone having a melting point of 82.5° C. as colorless crystalline powder.

Elementary Analysis:
Calcd for $C_{24}H_{26}N_2O_2 = 374.487$: C, 76.98; H, 7.00; N, 7.48 (%), Found: C, 76.93; H, 6.82; N, 7.47 (%).

EXAMPLE 3

3.1 g of 2-(3-chloro-2-methylpropyl)-4-phenyl-1(2H)-isoquinolone, 2 ml of dipropargylamine and 1.5 g of sodium iodide were added to 20 ml of methyl ethyl ketone, and the mixture was heated at reflux for 3 hours. Thereafter, the reaction mixture was filtered and the filtrate was concentrated under reduced pressure. The resulting residue was recrystallized from a mixture of ethanol and diethyl ether to obtain 1.8 g (50% yield) of 2-(3-N,N-dipropargylamino-2-methylpropyl)-4-phenyl-1(2H)-isoquinolone having a melting point of 139° C. as colorless prisms.

Elementary Analysis:
Calcd for $C_{25}H_{24}N_2O = 368.481$: C, 81.49; H, 6.57; N, 7.60 (%), Found: C, 81.29; H, 6.34; N, 7.69 (%).

EXAMPLE 4

A mixture of 6.6 g of 4-phenyl-1(2H)-isoquinolone, 2.9 g of 50% sodium hydride and 80 ml of dimethylformamide was stirred at 60° to 70° C. for 3 hours. 5.5 g of epichlorohydrin was then added dropwise to the reaction solution while cooling and stirring, and the mixture was then stirred at room temperature for 12 hours. The reaction solution was poured into ice-water, and the precipitated crystals were collected by filtration and washed with water. The crystals thus obtained were dissolved in 40 ml of dimethylformamide, 12 ml of diethylamine was added thereto and the mixture was heated at 100° C. for 5 hours in a sealed tube. The residue obtained after distilling off the solvent was dissolved in diethyl ether, and the solution was washed with water and extracted with 5% hydrochloric acid. The extract was rendered neutral with 10% aqueous solution of sodium hydroxide to precipitate crystals which were then collected by filtration and recrystallized from a mixture of ethyl acetate and petroleum ether to obtain 6.5 g (61% yield) of 2-(3-diethylamino-2-hydroxypropyl)-4-phenyl-1(2H)-isoquinolone having a melting point of 106° C. as colorless prisms.

Elementary Analysis:
Calcd for $C_{22}H_{26}N_2O_2 = 350.465$: C, 75.40; H, 7.48; N, 7.99 (%), Found: C, 75.49; H, 7.60; N, 7.82 (%).

EXAMPLE 5

6.2 g of 2-(3-chloro-2-methylpropyl)-4-phenyl-1(2H)-isoquinolone and 7.4 ml of diallylamine were added to 60 ml of xylene, and the mixture was heated at reflux for 16 hours. The solvent was then removed, and diethyl ether and 5% hydrochloric acid were added to the residue. The mixture was shaked well and the aqueous layer was separated. The aqueous layer was rendered alkaline with a 5% aqueous solution of sodium hydroxide, extracted with diethyl ether, and the ether layer was dried over potassium carbonate. The solvent was distilled off, and the residue was subjected to silica gel column chromatography to obtain 4.5 g (60% yield) of 2-(3-N,N-diallylamino-2-methylpropyl)-4-phenyl-1(2H)-isoquinolone as an oily substance.

Empirical Formula: $C_{25}H_{28}N_2O$,
Molecular Weight: 372.507,
Mass Spectrum m/e: 372 (M+)
Nuclear Magnetic Resonance Spectrum (CDCl$_3$) δ: 0.94 (3H, d, J=6 Hz CH$_3$), 2.35

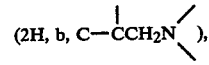

2.10–2.60

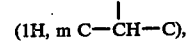

2.90–3.30 (4H, m, allyl CH$_2$), 3.72, 4.27

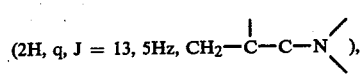

5.03 (2H, s, vinyl CH$_2$), 5.17 (2H, d, J=8 Hz, vinyl CH$_2$), 5.60–6.10 (2H, m vinyl CH), 7.02 (1H, s, aromatic C$_3$—H), 7.20–7.70 (8H, m, aromatic), 8.56 (1H, m, aromatic C$_8$—H).

EXAMPLES 6 TO 14

The following compounds were prepared in the same manner as described in Examples 1 to 5.

EXAMPLE 6

2-(2-N-methyl-N-benzylaminopropyl)-4-phenyl-1(2H)-isoquinolone. Recrystallized from ethanol, colorless needles, melting point: 149° C.

Elementary Analysis:
Calcd for $C_{26}H_{26}N_2O=382.510$: C, 81.64; H, 6.85; N, 7.32 (%), Found: C, 81.77; H, 6.80; N, 7.38 (%).

EXAMPLE 7

2-(3-N,N-diisopropylamino-2-hydroxypropyl)-4-phenyl-1(2H)-isoquinolone hydrochloride. Recrystallized from a mixture of ethanol and diethyl ether, colorless prisms, melting point of 218° C.

Elementary Analysis:
Calcd for $C_{21}H_{24}N_2O_2 \cdot HCl=372.899$: C, 67.64; H, 6.76; N, 7.51 (%), Found: C, 67.36; H, 6.64; N, 7.43 (%).

EXAMPLE 8

2-(3-N,N-dibutylamino-2-hydroxypropyl)-4-phenyl-1(2H)-isoquinolone hydrochloride. Recrystallized from a mixture of ethanol and petroleum ether, colorless needles, melting point: 171° C.

Elementary Analysis:
Calcd for $C_{26}H_{34}N_2O_2 \cdot HCl=443.034$: C, 70.49; H, 7.96; N, 6.32 (%), Found: C, 70.50; H, 7.93; N, 6.26 (%).

EXAMPLE 9

2-(3-N,N-diisobutylamino-2-hydroxypropyl)-4-phenyl-1(2H)-isoquinolone maleate. Recrystallized from a mixture of ethanol and diethyl ether, colorless prisms, melting point: 144.5° C.

Elementary Analysis:
Calcd for $C_{26}H_{34}N_2O_2 \cdot C_4H_4O_4=522.647$: C, 68.94; H, 7.33; N, 5.36 (%), Found: C, 69.15; H, 7.34; N, 5.19 (%).

EXAMPLE 10

2-(2-N-benzylaminopropyl)-4-phenyl-1(2H)-isoquinolone, Recrystallized from a mixture of ethyl acetate and petroleum ether, colorless needles, melting point: 118° C.

Elementary Analysis:
Calcd for $C_{25}H_{24}N_2O=368.483$: C, 81.49; H, 6.57; N, 7.60 (%), Found: C, 81.44; H, 6.56; N, 7.52 (%).

EXAMPLE 11

2-(2-N-benzylaminopropyl)-4-phenyl-1(2H)-isoquinolone maleate. Recrystallized from a mixture of ethanol and diethyl ether, colorless prisms, melting point: 161° C.

Elementary Analysis:
Calcd for $C_{25}H_{24}N_2O \cdot C_4H_4O_4=484.557$: C, 71.88; H, 5.82; N, 5.78 (%), Found: C, 72.02; H, 5.76; N, 5.88 (%).

EXAMPLE 12

2-(2-N-allylaminopropyl)-4-phenyl-1(2H)-isoquinolone. Colorless oily substance, boiling point: 215° C./4 mmHg (bath temperature).

Elementary Analysis:
Calcd for $C_{21}H_{22}N_2O=318.422$: C, 79.21; H, 6.96; N, 8.80 (%), Found: C, 79.39; H, 7.07; N, 8.71 (%).

EXAMPLE 13

2-(2-N-allylaminopropyl)-4-phenyl-1(2H)-isoquinolone maleate. Recrystallized from a mixture of ethanol and diethyl ether, colorless plates, melting point: 177° C.

Elementary Analysis:
Calcd for $C_{21}H_{22}N_2O \cdot C_4H_4O_4=434.496$: C, 69.11; H, 6.03; N, 6.45 (%), Found: C, 69.15; H, 5.96; N, 6.40 (%).

EXAMPLE 14

2-(2-N-ethyl-N-benzylaminopropyl)-4-phenyl-1(2H)-isoquinolone. Recrystallized from a mixture of ethyl acetate and petroleum ether, colorless prisms, melting point: 106° C.

Elementary Analysis:
Calcd for $C_{27}H_{28}N_2O=396.537$: C, 81.78; H, 7.12; N, 7.06 (%), Found: C, 81.72; H, 7.14; N, 6.97 (%).

EXAMPLE 15

A. 29.8 g of 2-(2-chloropropyl)-4-phenyl-1(2H)-isoquinolone was mixed with 20 ml of benzylamine, and the mixture was heat-melted in a nitrogen stream. After completion of the reaction, the mixture was dissolved in methanol while hot, and the solution was poured into crashed ice. The resulting precipitate was collected by filtration, washed with water, dried and recrystallized from a mixture of ethyl acetate and petroleum ether to obtain 30.2 g (82% yield) of 2-(2-benzylaminopropyl)-4-phenyl-1(2H)-isoquinolone having a melting point of 118° C.

Elementary Analysis:
Calcd for $C_{25}H_{24}N_2O=368.483$: C, 81.49; H, 6.57; N, 7.60 (%), Found: C, 81.61; H, 6.66; N, 7.59 (%).

B. 36.8 g of 2-(2-benzylaminopropyl)-4-phenyl-1(2H)-isoquinolone preapred as described above, 12 g of 5% palladium-carbon, 50 ml of glacial acetic acid and 200 ml of ethanol were mixed, and the mixture was catalytically reduced while introducing hydrogen gas into the mixture at 60° to 70° C. After completion of the reduction reaction, the mixture was filtered, and the solvent was distilled off from the filtrate. The resulting residue was dissolved in 5% hydrochloric acid and the solution was washed with ethyl acetate. The aqueous layer was separated and rendered neutral with a 10% aqueous solution of sodium hydroxide. The resulting precipitate was filtered and recrystallized from a mixture of ethyl acetate and petroleum ether to obtain 20.9 g (75% yield) of 2-(2-aminopropyl)-4-phenyl-1(2H)-isoquinolone having a melting point of 104° C. as colorless prisms.

Elementary Analysis:
Calcd for $C_{18}H_{18}N_2O=278.357$: C, 77.67; H, 6.52; N, 10.06 (%), Found: C, 77.79; H, 6.57; N, 10.01 (%).

C. 6 g of maleic acid was added to 14 g of 2-(2-aminopropyl)-4-phenyl-1(2H)-isoquinolone prepared as described above in 80 ml of ethyl acetate, and the mixture was stirred while warming. The crystals precipitated upon cooling were collected by filtration and recrystallized from a mixture of ethanol and ethyl acetate to obtain 16.5 g of 2-(2-aminopropyl)-4-phenyl-1(2H)-isoquinolone maleate having a melting point of 187° C. as colorless prisms.

Elementary Analysis:
Calcd for $C_{18}H_{18}N_2O \cdot C_4H_4O_4=394.431$: C, 66.99; H, 5.62; N, 7.10 (%), Found: C, 67.07; H, 5.58; N, 7.01 (%).

EXAMPLE 16

4.2 g of 2-(2-aminopropyl)-4-phenyl-1(2H)-isoquinolone, 2.7 g of ethyl chlorocarbonate, 4.1 g of potassium carbonate and 60 ml of ethanol were mixed and stirred at room temperature for 3 hours. The solvent was then distilled off, and the residue was extracted with dichloromethane. The crystals obtained by distilling off the solvent were recrystallized from ethanol to obtain 3 g (57% yield) of 2-(2-ethoxycarbonylaminopropyl)-4-phenyl-1(2H)-isoquinolone having a melting point of 182° C. as colorless prisms.

Elementary Analysis:

Calcd for $C_{21}H_{22}N_2O_3 = 350.421$: C, 71.98; H, 6.33; N, 7.99 (%), Found: C, 71.92; H, 6.36; H, 7.91 (%).

EXAMPLE 17

5 g of 2-(2-aminopropyl)-4-phenyl-1(2H)-isoquinolone, 1.2 g of methyl isocyanate and 60 ml of toluene were mixed and stirred at room temperature for 3 hours. 60 ml of petroleum ether was then added to the reaction mixture and the mixture was thoroughly mixed, followed by allowing to stand. The precipitated crystals were collected by filtration and recrystallized from ethanol to obtain 5.1 g (80% yield) of 2-(2-N'-methylureidopropyl)-4-phenyl-1(2H)-isoquinolone monohydrate having a melting point of 180° C. as colorless needles.

Elementary Analysis:

Calcd for $C_{20}H_{21}N_3O_2 \cdot H_2O = 353.425$: C, 67,97; H, 6.56; N, 11.89 (%), Found: C, 68.02; H, 6.54; N, 11.70 (%).

EXAMPLE 18

A mixture of 5 g of 2-(2-aminopropyl)-4-phenyl-1(2H)-isoquinolone, 10 ml of acetic anhydride and 10 ml of glacial acetic acid was warmed on a water bath for 3 hours and the resulting reaction mixture was poured into ice-water. The precipitated crystals were extracted with dichloromethane, and the extract was thoroughly washed successively with a 5% aqueous solution of sodium hydroxide and water, and then dried over anhydrous sodium sulfate. The crystals obtained by distilling off the solvent was recrystallized from ethanol to obtain 4.8 g (83% yield) of 2-(2-acetamidopropyl-4-phenyl-1(2H)-isoquinolone having a melting point of 177° C. as colorless needles.

Elementary Analysis:

Calcd for $C_{20}H_{20}N_2O_2 = 320.395$: C, 74.98; H, 6.29; N, 8.74 (%), Found: C, 75.10; H, 6.31; N, 8.71 (%).

EXAMPLE 19

A. A solution of 13.6 g of chloroacetyl chloride in 50 ml of dichloromethane was added dropwise to a mixture of 27.8 g of 2-(2-aminopropyl)-4-phenyl-1(2H)-isoquinolone, 150 ml of dichloromethane and 100 ml of a 10% aqueous solution of sodium hydroxide while cooling at 5° C. with stirring. After 30 minutes, dichloromethane layer was separated, washed with water and dried over sodium sulfate. The solvent was then removed and the resulting crystals were recrystallized from ethyl acetate to obtain 30.5 g (86% yield) of 2-(2-chloroacetamidopropyl)-4-phenyl-1(2H)-isoquinolone having a melting point of 140° C. as colorless prisms.

Elementary Analysis:

Calcd for $C_{20}H_{19}ClN_2O_2 = 354.840$: C, 67.70; H, 5.40; N, 7.89 (%), Found: C, 67.66; H, 5.47; N, 7.82 (%).

B. A mixture of 6 g of 2-(2-chloroacetamidopropyl)-4-phenyl-1(2H)-isoquinolone prepared as described above, 5 g of diethylamine and 50 ml of ethanol was heated at reflux for 5 hours, and the solvent was then distilled off. The resulting residue was dissolved in dichloromethane, and the solution was washed with water and dried over anhydrous sodium sulfate. The solvent was then distilled off, and the resulting crystals were recrystallized from a mixture of ethyl acetate and petroleum ether to obtain 5.7 g (86% yield) of 2-(2-N,N-diethylaminoacetamidopropyl)-4-phenyl-1(2H)-isoquinolone having a melting point of 138° C. as colorless needles.

Elementary Analysis:

Calcd for $C_{24}H_{29}N_3O_2 = 391.518$: C, 73.63; H, 7.47; N, 10.73 (%), Found: C, 73.69; H, 7.52; N, 10.75 (%).

EXAMPLE 20

5.2 g of 2-(2-chloroacetamidopropyl)-4-phenyl-1(2H)-isoquinolone was dissolved in 100 ml of dichloromethane, and a solution of 0.46 g of sodium metal dissolved in 10 ml of N,N-diethylaminoethanol was added thereto, followed by stirring the resulting mixture overnight at room temperature. Water was added to the reaction mixture, and the dichloromethane layer was separated, washed with water and dried over anhydrous sodium sulfate. The solvent was distilled off, and the resulting residue was dissolved in diethyl ether. The solution was extracted with 5% hydrochloric acid and the aqueous layer was rendered neutral with a 10% aqueous solution of sodium hydroxide. The precipitated crystals were collected by filtration and recrystallized from a mixture of ethyl acetate and petroleum ether to obtain 3 g (46% yield) of 2-(2-N,N-diethylaminoethoxyacetamidopropyl)-4-phenyl-1(2H)-isoquinolone having a melting point of 99° C. as colorless needles.

Elementary Analysis:

Calcd for $C_{26}H_{33}N_3O_3 = 435.571$: C, 71.70; H, 7.64; N, 9.65 (%), Found: C, 71.83; H, 7.63; N, 9.57 (%).

EXAMPLE 21

7.1 g of 2-(2-chloroacetamidopropyl)-4-phenyl-1(2H)-isoquinolone, 3.7 g of phthalimide and 3.7 g of potassium carbonate were added to 50 ml of dimethylformamide, and the mixture was stirred at 80° C. for 5 hours. The resulting reaction mixture was poured into water and the precipitated crystals were collected by filtration, washed with water and dried in air. The resulting crystals and 2 g of hydrazine hydrate were added to 100 ml of ethanol and the mixture was heated at reflux for 3 hours. After allowing the mixture to cool, 5 ml of concentrated hydrochloric acid was added to the resulting reaction mixture and the mixture was stirred for 5 hours. The solvent was then distilled off, and water was added to the residue, followed by thoroughly stirring. The mixture was filtered and the filtrate was rendered neutral with a 10% aqueous solution of sodium hydroxide. The precipitated was extracted with dichloromethane, and the extract was washed with water and dried. The solvent was distilled off and the resulting crystals were recrystallized from a mixture of ethyl acetate and petroleum ether to obtain 2.3 g (34% yield) of 2-(2-aminoacetamidopropyl)-4-phenyl-1(2H)-isoquinolone having a melting point of 141° C. as colorless needles.

Elementary Analysis:

Calcd for $C_{20}H_{21}N_3O_2 = 335.409$: C, 71.62; H, 6.31; N, 12.53 (%), Found: C, 71.68; H, 6.21; N, 12.44 (%).

EXAMPLE 22

A mixture of 2.8 g of 2-(2-aminopropyl)-4-phenyl-1(2H)-isoquinolone, 1.9 g of diethylcarbamoyl chloride and 1.1 g of pyridine was heated at 90° C. for 1 hour. After allowing the mixture to cool, ethyl acetate was added to the reaction mixture which was then washed with water and dried. The solvent was distilled off and the residue was recrystallized from a mixture of ethyl acetate and petroleum ether to obtain 1.6 g (42% yield) of 2-(2-N',N'-diethylureidopropyl)-4-phenyl-1(2H)-isoquinolone having a melting point of 132° C. as pale yellow prisms.

Elementary Analysis:

Calcd for $C_{23}H_{27}N_3O_2=377.491$: C, 73.18; H, 7.21; N, 11.13 (%), Found: C, 73.31; H, 7.27; N, 11.14 (%).

EXAMPLES 23 TO 35

The following compounds were prepared in the same manner as described in Examples 15 to 22.

EXAMPLE 23

2-(2-aminoacetamidopropyl)-4-phenyl-1(2H)-isoquinolone maleate. Recrystallized from ethanol, colorless prisms, melting point: 174° C.

Elementary Analysis:

Calcd for $C_{20}H_{21}N_3O_2.C_4H_4O_4=451.483$: C, 63.85; H, 5.58; N, 9.31 (%), C, 63.96; H, 5.51; N, 9.20 (%).

EXAMPLE 24

2-{2-(4-morpholino)acetamidopropyl}-4-phenyl-1(2H)-isoquinolone. Recrystallized from a mixture of ethanol and ethyl acetate, colorless prisms, melting point: 189° C.

Elementary Analysis:

Calcd for $C_{24}H_{27}N_3O_3=405.501$: C, 71.09; H, 6.71; N, 10.36 (%), Found: C, 71.24; H, 6.79; N, 10.41 (%).

EXAMPLE 25

2-{2-(4-morpholino)acetamidopropyl}-4-phenyl-1(2H)-isoquinolone maleate. Recrystallized from a mixture of ethanol and diethyl ether, colorless needles, melting point: 122° C.

Elementary Analysis:

Calcd for $C_{24}H_{27}N_3O_3.C_4H_4O_4=521.575$: C, 64.48; H, 5.99; N, 8.06 (%), Found: C, 64.41; H, 5.92; N, 7.93 (%).

EXAMPLE 26

2-(2-N,N-dimethylaminoacetamidopropyl)-4-phenyl-1(2H)-isoquinolone. Recrystallized from a mixture of ethyl acetate and petroleum ether, colorless prisms, melting point: 164° C.

Elementary Analysis:

Calcd for $C_{22}H_{25}N_3O_2=363.463$: C, 72.70; H, 6.93; N, 11.56 (%), Found: C, 72.62; H, 6.98; N, 11.64 (%).

EXAMPLE 27

2-(2-N,N-dimethylaminoacetamidopropyl)-4-phenyl-1(2H)-isoquinolone maleate. Recrystallized from a mixture of ethanol and diethyl ether, colorless prisms, melting point: 148° C.

Elementary Analysis:

Calcd for $C_{22}H_{25}N_3O_2.C_4H_4O_4=479.538$: C, 65.12; H, 6.10; N, 8.76 (%), Found: C, 65.26; H, 6.03; N, 8.82 (%).

EXAMPLE 28

2-(2-N,N-diethylaminoacetamidopropyl)-4-phenyl-1(2H)-isoquinolone maleate. Recrystallized from a mixture of ethanol and diethyl ether, colorless needles, melting point: 140° C.

Elementary Analysis:

Calcd for $C_{24}H_{29}N_3O_2.C_4H_4O_4=507.592$: C, 66.26; H, 6.55; N, 8.28 (%), Found: C, 66.35; H, 6.55; N, 8.15 (%).

EXAMPLE 29

2-(2-N,N-diethanolaminoacetamidopropyl)-4-phenyl-1(2H)-isoquinolone. Recrystallized from a mixture of ethanol and ethyl acetate, colorless prisms, melting point: 129° C.

Elementary Analysis:

Calcd for $C_{24}H_{29}N_3O_4=423.516$: C, 68.07; H, 6.90; N, 9.92 (%), Found: C, 68.12; H, 6.93; N, 9.82 (%).

EXAMPLE 30

2-(2-N,N-diethanolaminoacetamidopropyl)-4-phenyl-1(2H)-isoquinolone hydrochloride. Recrystallized from a mixture of ethanol and diethyl ether, colorless crystalline powder, melting point: 158° C.

Elementary Analysis:

Calcd for $C_{24}H_{29}N_3O_4.HCl=459.977$: C, 62.67; H, 6.57; N, 9.14 (%), Found: C, 62.70; H, 6.55; N, 9.07 (%).

EXAMPLE 31

2-(2-N,N-diallylaminoacetamidopropyl)-4-phenyl-1(2H)-isoquinolone. Recrystallized from a mixture of ethyl acetate and petroleum ether, colorless flakes, melting point: 132° C.

Elementary Analysis:

Calcd for $C_{26}H_{29}N_3O_2=415.540$: C, 75.15; H, 7.03; N, 10.11 (%), Found: C, 75.21; H, 7.00; N, 10.16 (%).

EXAMPLE 32

2-(2-N,N-diallylaminoacetamidopropyl)-4-phenyl-1(2H)-isoquinolone maleate. Recrystallized from a mixture of ethanol and diethyl ether, colorless needles, melting point: 105° C.

Elementary Analysis:

Calcd for $C_{26}H_{29}N_3O_2.C_4H_4O_4=531.614$: C, 67.78; H, 6.26; N, 7.90 (%), Found: C, 67.91; H, 6.20; N, 7.95 (%).

EXAMPLE 33

2-[2-(4-methyl-1-piperazino)acetamidopropyl]-4-phenyl-1(2H)-isoquinolone. Recrystallized from a mixture of ethanol and ethyl acetate, colorless needles, melting point: 186° C.

Elementary Analysis:

Calcd for $C_{25}H_{30}N_4O_2=418.543$: C, 71.74; H, 7.22; N, 13.39 (%), Found: C, 71.78; H, 7.15; N, 13.41 (%).

EXAMPLE 34

2-[2-(4-methylpiperazin-1-yl)acetamidopropyl]-4-phenyl-1(2H)-isoquinolone dimaleate. Recrystallized from a mixture of methanol and diethyl ether, colorless needles, melting point: 183° C.

Elementary Analysis:

Calcd for $C_{25}H_{30}N_4O_2.2C_4H_4O_4=650.692$: C, 60.91; H, 5.89; N, 8.61 (%), Found: C, 61.04; H, 5.96; N, 8.46 (%).

EXAMPLE 35

2-(2-N,N-diethylaminoethoxyacetamidopropyl)-4-phenyl-1(2H)-isoquinoline hydrochloride. Recrystallized from ethanol, colorless needles, melting point: 212° C.

Elementary Analysis:

Calcd for $C_{26}H_{33}N_3O_3.HCl=472.032$: C, 66.16; H, 7.26; N, 8.90 (%), Found: C, 66.25; H, 7.20; N, 8.85 (%).

The pharmacological activities, acute toxicity and pharmaceutical preparations are illustrated below with respect to typical examples of the compounds of this invention having the formula (I) and the acid addition salts thereof in comparison with typical known compounds.

Compounds of Present Invention

Compound A: 2-(2-N,N-diallylaminopropyl)-4-phenyl-1(2H)-isoquinolone maleate (prepared in Example 1)

Compound B: 2-(3-N,N-diallylamino-2-methylpropyl)-4-phenyl-1(2H)-isoquinolone hydrochloride (prepared in Example 5)

Compound C: 2-(2-aminopropyl)-4-phenyl-1(2H)-isoquinolone maleate (prepared in Example 15)

Anti-ulcer Activity (1) Stress Ulcer

The test compound was administered orally to Wistar male rats (body weight, 200 to 230 g) and 30 minutes thereafter the rats were tied up with a steel wire and dipped in water at 23° C. in a tank to the level of the xiphisternum of rats. After leaving the rats in water for 7 hours, the rats were sacrificed and the stomach was extracted. 10 ml of a 1% formalin solution was injected into the stomach cavity and the stomach was dipped in a 1% formalin solution for 15 minutes to semi-harden the stomach. The stomach was excised along the greater curvature thereof and the ulcer generated in the portion of corpus ventriculi was observed to determine the ulcerous index in terms of the total length of erosion generated (mm). The results obtained are shown in Table 1 below. As is apparent from the results, Compounds A and B inhibit the ulcer generation caused by water-dipping restriction stress at the dose of 50 mg/kg.

TABLE 1

| Test Compound | Dose (mg/kg) | Number of Rats | Ulcerous Index (mm) | Percent Inhibition (%) |
|---|---|---|---|---|
| Control | | 6 | 26.3 ± 11.54 | |
| Compound A | 50 | 6 | 10.5 ± 6.22* | 62.2 |
| Compound A | 50 | 6 | 6.8 ± 3.19* | 75.5 |

Mean ± Standard Deviation
*p < 0.01

(2) Stress Ulcer

The test compound was administered orally to Wistar male rats (body weight, 180 to 200 g) which fasted for 18 hours before testing. 30 minutes thereafter, stress was loaded to the rats in a stress cage by dipping the cage into water at 23° C. to the level of the xiphisternum of rats. After leaving the rats in water for 7 hours, the rats were sacrificed and the stomach was extracted. The stomach was then worked up in the same manner as above to determine the ulcerous index. The results obtained are shown in Table 2 below. As is apparent from the results, Compound C exhibits a stress ulcer inhibitory activity substantially equivalent to that of propantheline bromide.

TABLE 2

| Test Compound | Dose (mg/kg) | Number or Rats | Ulcerous Index (mm) | Precent Inhibition (%) |
|---|---|---|---|---|
| Control | | 7 | 30.9 ± 11.04 | |
| Compound C | 25 | 7 | 14.6 ± 8.70* | 52.8 |
| Propantheline Bromide | 25 | 7 | 14.9 ± 10.67** | 51.9 |

Mean ± Standard Deviation
*p < 0.01
**p < 0.05

(3) Aspirin Ulcer

The pylorus of Wistar male rats (body weight, 230 to 250 g) which fasted for 24 hours was ligated and, immediately thereafter, the test compound was administered into the duodenum. 15 hours thereafter, acetylsalicylic acid (Aspirin) was administered orally at a dose of 100 mg/kg. Seven hours after administration of acetylsalicylic acid, the rats were sacrificed and the gastric juice was collected. the stomach was then worked up in the same manner as above to determine the ulcerous index. The results obtained are shown in Table 3 below. As is apparent from the results, Compound A inhibits the aspirin-induced ulcer at dose levels of 10, 25, 50 mg/kg, with dependency upon dose.

TABLE 3

| Test Compound | Dose (mg/kg) (i.d.) | Number of Rats | Ulcerous Index (mm ± SE) | Percent Inhibition (%) |
|---|---|---|---|---|
| Control | | 13 | 59.90 ± 4.13 | |
| Compound A | 10 | 6 | 42.28 ± 2.56* | 29.41 |
| Compound A | 25 | 6 | 34.15 ± 4.37** | 42.98 |
| Compound A | 50 | 6 | 25.44 ± 3.41** | 57.52 |

*p < 0.01
**p < 0.001

Blood flow Increasing Activity on Stomach Mucous Membrane (Aminopyrin Clearance Method)

The cardia and pylorus of Wistar male rats (body weight, 250 to 300 g) which fasted 16 hours before abdominal section were ligated under urethane anesthesia, and a cannula was inserted into the preventriculus. In order to keep the stomach in normal state, the cannula was fixed externally and the incised abdomen was closed. Separately, a cannula filed with heparin was inserted into carotid artery.

After operation, the inside of stomach was thoroughly washed with warm physiological saline solution, and 2 ml of a gastric juice (prepared by adjusting a 5% aqueous solution of mannitol to a pH 3.5 with 0.15 N hydrochloric acid, hereinafter the same) was poured into the stomach. Then, aminopyrin was administered via femoral vein at a dose of 30 mg/kg and 30 minutes thereafter aminopyrin was continuously administered at a rate of 6.6 mg/kg/hour. 45 minutes after the commencement of continuous administration of aminopyrin, 2 ml of the gastric juice warmed at 37° C. was poured into the stomach and collected after 15 minutes.

The collection of gastric juice was conducted at 15 minute intervals and 2 ml of the gastric juice was poured into the stomach between the collections. The total volume of gastric juice collected was 5 ml; 2 ml of the gastric juice was first drawn by syringe pump, 2 ml of the gastric juice was poured into the stomach and then drawn, and finally 1 ml of gastric juice was poured into the stomach and then drawn. 2 ml of the gastric juice drawn (5 ml) was presented to quantitative determination.

Sixty minutes after the commencement of continuous administration of aminopyrin, 0.5 ml of blood was drawn from the carotid artery. Thereafter, 0.5 ml of blood was drawn twice (intermediate and end points of the continuous administration of aminopyrin).

The test compound was administered intravenously immediately after the third collection of gastric juice.

After collecting the gastric juice and blood samples, the stomach was extracted and weighed to determine the total weight of the stomach tissue.

Then, the amount of aminopyrin in the blood sample and the gastric juice was determined quantitatively and the volume of blood flow in the stomach mucous membrane per gram of the stomach tissue per minute was calculated.

As a result, Compound A was found to have a significance increasing activity on the stomach mucous membrane blood flow 15, 30 and 45 minutes after intravenous administration of 3 mg/kg. The percent increase in blood flow became maximum after 30 minutes and was found to be about 50%.

On the other hand, cetraxate hydrochloride, which is known to have a stomach mucous membrane blood flow increasing activity, was also tested in the same manner as described above and showed a significant blood flow increasing activity 15 and 30 minutes after intravenous administration at a dose of 20 mg/kg. However, the percent increase in blood flow was found to be about 35% at 15 and 30 minutes.

Recovery Activity on Blood Flow Decrease in Stomach Mucous Membrane by Blood Drawing Wistar male rats (body weight, 250 to 280 g) fasted for 24 hours and the blood flow in stomach mucous membrane was determined by the aminopyrin clearance method as described above under urethane anesthesia. After determination of blood flow, a blood sample was drawn in an amount equivalent to 3% of the body weight and, 5 minutes thereafter, the blood sample was reinstated. The blood flow was then determined at an interval of 15 minutes. The test compound was administered intravenously 15 minutes after the blood drawing.

The results obtained are shown in Table 4 below. It is apparent from the results that Compound C shows a significant recovery activity on blood flow decrease in stomach mucous membrane by blood drawing.

TABLE 4

| | Recovery Activity on Blood Flow Decrease in Stomach Mucous Membrane by Blood Drawing | | | | | | |
|---|---|---|---|---|---|---|---|
| | Dose | Number of | Blood Flow in Mucous Membrane (%) | | | | |
| Test Compound | (mg/kg) | Rats | 0 | 15 min. | 30 min. | 45 min. | 60 min. |
| Control | | 3 | 100 | 59.0 ± 15.3 | 50.5 ± 28.3 | 50.7 ± 32.8 | 58.0 ± 40.5 |
| Compound C | 10 | 3 | 100 | 88.4 ± 36.9 | 92.7 ± 23.5 | 98.2 ± 10.2* | 101.4 ± 8.8 |

Mean ± Standard Deviation
*p < 0.05

Anti-hypertensive Activity

Cats weighing 3 to 5 kg were anesthetized by intraperitoneal administration of urethane at a dose of 1.5 g/kg. The test compound was administered through a catheter into a femoral vein and the blood pressure was determined by a pressure transducer through a catheter inserted into the femoral artery.

As a result, each of Compounds A and B exhibits a blood pressure lowering activity to a degree of 50 to 70 mmHg at a dose of 5 to 10 mg/kg. The blood pressure lowering activity lasts for more than 2 hours.

Gastric Secretion Inhibitory Activity

The pylorus of Wistar male rats (body weight, 180 to 200 g) which fasted for 24 hours was ligated under ether anesthesia and, immediately thereafter, the test compound was administered into the duodenum. Five hours after the administration, the rats were sacrificed and gastric juice was collected. The volume and the pH value of the gastric juice and the degree of acid secretion were then determined. The results obtained are shown in Table 5 below. As is apparent from the results, Compound C exhibits a gastric secretion inhibitory activity substantially equivalent to that of propantheline bromide but higher than that of Cimetidine.

TABLE 5

| | Gastric Secretion Inhibitory Activity | | | | | |
|---|---|---|---|---|---|---|
| Test Compound | Dose (mg/kg) | Number of Rats | Amount of Gastric Juice (ml) | Percent Inhibition (%) | Amount of Output Secretion (μ Eq.) | Precent Inhibition (%) |
| Control | | 10 | 3.36 ± 1.14 | | 288.1 ± 126.69 | |
| Compound C | 25 | 10 | 1.54 ± 0.58** | 54.2 | 126.0 ± 40.42** | 56.3 |
| Propantheline Bromide | 25 | 10 | 1.46 ± 0.63** | 56.5 | 118.8 ± 63.51** | 58.8 |
| Cimetidine | 25 | 10 | 2.26 ± 0.85 | 32.7 | 136.6 ± 74.19* | 52.6 |

Mean ± Standard Deviation
**p < 0.01
*p < 0.05

Preparation Examples

1. Granules

| | |
|---|---|
| Compound A | 200 mg |
| Lactose | 500 mg |
| Corn Starch | 280 mg |
| Hydroxypropylcellulose | 20 mg |
| | 1,000 mg per pack |

The granule preparation was prepared in a conventional manner using the above formulation.

2. Tablets

| | |
|---|---|
| Compound A | 100 mg |
| Lactose | 85 mg |
| Crystalline Cellulose | 50 mg |
| Hydroxypropylcellulose | 30 mg |
| Talc | 4 mg |
| Magnesium Stearate | 1 mg |
| | 270 mg per tablet |

The tablet preparation was prepared in a conventional manner using the above formulation.

3. Capsules

| | |
|---|---|
| Compound B | 200 mg |

-continued

3. Capsules

| Lactose | 100 mg |
|---|---|
| Crystalline Cellulose | 18 mg |
| Magnesium Stearate | 2 mg |
| | 400 mg per capsule |

The tablet preparation was prepared in a conventional manner using the above formulation.

What is claimed is:

1. A 1(2H)-isoquinolone compound represented by the formula (I)

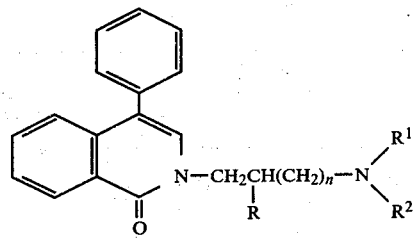

(I)

wherein n is 0 or an integer of 1, R represents a methyl group or a hydroxy group, $R^1$ represents a hydrogen atom, an alkyl group having 1 to 4 carbon atoms, an alkenyl group having 3 to 4 carbon atoms, or an alkynyl group having 3 to 4 carbon atoms, and $R^2$ represents a hydrogen atom, an alkyl group having 1 to 4 carbon atoms, an alkenyl group having 3 to 4 carbon atoms, an alkynyl group having 3 to 4 carbon atoms, a benzyl group, an ethoxycarbonyl group, a mono- or dialkylcarbamoyl having 1 to 4 carbon atoms in each alkyl group, an acetyl group, a mono- or dialkylaminoethoxyacetyl group or a group of the formula

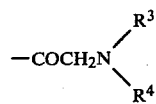

wherein $R^3$ and $R^4$, which may be the same or different, each represents a hydrogen atom, an alkyl group having 1 to 4 carbon atoms, a hydroxyalkyl group having 2 to 4 carbon atoms or an allyl group, or $R^3$ and $R^4$, when taken together with nitrogen atom to which they are attached, represent a heterocyclic group selected from the group consisting of a pyrrolidino group, a piperazino group, a 4-methylpiperazino group, a piperidino group and a morpholino group, with the proviso that, when R represents a methyl group,

cannot be a monoalkylamino group or a dialkylamino group and when R represents a hydroxy group, n represents an integer of 1; and the acid addition salt thereof.

2. 2-(2-N,N-Diallylaminopropyl)-4-phenyl-1(2H)-isoquinoline and an acid addition salt thereof, according to claim 1.

3. 2-(3-N,N-Diallylamino-2-methylpropyl-4-phenyl-1(2H)-isoquinolone and an acid addition salt thereof, according to claim 1.

4. 2-(2-Aminopropyl)-4-phenyl-1(2H)-isoquinolone and an acid addition salt thereof, according to claim 1.

* * * * *